(12) United States Patent
Miura et al.

(10) Patent No.: US 7,411,078 B2
(45) Date of Patent: Aug. 12, 2008

(54) METHOD FOR PRODUCING FURAN-2,5-DICARBOXYLIC ACID

(75) Inventors: Toshinari Miura, Kawasaki (JP); Hirokazu Kakinuma, Kawasaki (JP); Takenobu Kawano, Kawasaki (JP); Hirohide Matsuhisa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/683,271

(22) Filed: Mar. 7, 2007

(65) Prior Publication Data

US 2007/0232815 A1    Oct. 4, 2007

(30) Foreign Application Priority Data

Mar. 28, 2006  (JP)  .............................. 2006-088520

(51) Int. Cl.
  *C07D 307/02*   (2006.01)
(52) U.S. Cl. ........................ 549/484; 549/485; 549/488
(58) Field of Classification Search ................. 549/484, 549/485, 488
  See application file for complete search history.

(56) References Cited

U.S. PATENT DOCUMENTS 3,326,944 A    6/1967  Lew
4,977,283 A    12/1990 Leupold et al.

FOREIGN PATENT DOCUMENTS

JP     2-088569 A    3/1990

OTHER PUBLICATIONS

Shunichi Morikawa, "Synthesis of 2,5-Furandicaroxaldehyde from 5-Hydroxymethylfural," *Annual Report of the Noguchi Institute*, 1979, p. 20-27 (with English translation).
Toni El Hajj et al., "Synthèse de l'hydroxyméthyl-5 furanne carboxaldéhyde-2 et de ses dérivés par traitement acide de sucres sur résines échangeuses d'ions", *Bulletin de la Société Chimique de France*, 1987 No. 5, p. 855-60.
J. Lewkowski, "Convenient Synthesis of Furan-2,5-dicarboxylic Acid and Its Derivatives", 75 *Polish J. Chem.* 1943-46 (2000).

*Primary Examiner*—Sikarl A Witherspoon
(74) *Attorney, Agent, or Firm*—Fitzpatrick, Cella, Harper & Scinto

(57) ABSTRACT

A method for producing furan-2,5-dicarboxylic acid (FDCA) is provided which can efficiently and quantitatively producing FDCA under mild conditions, without employing an expensive catalyst and with a reduced energy consumption. A furan ring compound having two functional groups selected from a hydroxymethyl group, a formyl group and a carboxyl group in the 2- and 5-positions of the furan ring, is oxidized with a metal permanganate in an alkaline environment to produce furan-2,5-dicarboxylic acid. Advantageously, the alkaline environment contains at least one of alkali metal hydroxides and alkali earth metal hydroxides, and the oxidation is performed at a temperature of from 1 to 50° C. by adding the permanganate metal salt to the alkaline aqueous solution containing the furan ring compound.

11 Claims, No Drawings

METHOD FOR PRODUCING FURAN-2,5-DICARBOXYLIC ACID

BACKGROUND OF THE INVENTION

1. Field of the Invention

The present invention relates to a producing method for furan-2,5-dicarboxylic acid, capable of producing furan-2,5-dicarboxlic acid efficiently under mild conditions and with a high yield.

Description of the Related Art

Furan-2,5 -dicarboxylic acid (hereinafter abbreviated as FDCA) is valuable as an intermediate for pharmaceuticals, agrochemicals, insecticides, antibacterial agents, fragrances and so forth. For synthesizing furan-2,5-dicarboxylic acid, there is reported a method of utilizing a catalyst including platinum carried on active carbon and dropwise adding 5-HMF into a basic aqueous solution while bubbling oxygen, thereby carrying out an oxidation (see U.S. Pat. No 3,326,944, page 3, Examples 3 and 4; Japanese Patent Application Laid-open No. H02-088569, page 4, Example 3; and U.S. Pat. No. 4,977,283, page 4, Example 3). Also, a method is reported utilizing a catalyst including platinum carried on active carbon and oxidizing 5-HMF with oxygen in diethylene glycol dimethyl ether/water (see Japanese Patent Application Laid-Open No. H02-088569 and U.S. Pat. No. 4,977,283). Further, a method of oxidizing 5-HMF with nitric acid or dinitrogen tetroxide in dimethyl sulfoxide (DMSO) is reported (see Annual report of the Noguchi Institute, vol. 22, pages 24 to 26). Further, there is reported a method of oxidizing 5-HMF with potassium permanganate utilizing pyridine as a base (see Toni EL HAJJ et al., Bulletin de la Societe de France, vol. 5, 1987 "Synthese de l'hydroxymethyl-5 furanne carboxaldehyde-2 et de ses derives par traitement acide de sucres sur resines echangeuses d'ions", p.860, experimental C). In addition, there is reported a method of dehydrating mucic acid by p-toluenesulfonic acid (see Lewkowski J., Polish Journal of Chemistry, vol. 75, 2001 "Convenient Synthesis of Furan-2,5-dicarboxylic Acid and Its Derivatives" p. 1944).

However, the methods described in U.S. Pat. No. 3,326,944, Japanese Patent Application Laid-Open No. H02-088569 and U.S. Pat. No. 4,977,283 have problems in that a large amount of a precious metal catalyst is used, the platinum catalyst is liable to deteriorate under the alkaline conditions, and the catalyst has a low reusability. Also, long reaction time results in an increased production cost and a low production efficiency. Furthermore, these methods are difficult to apply on an industrial scale. In addition, the method of utilizing a catalyst including platinum carried on active charcoal and oxidizing 5-HMF with oxygen in diethylene glycol dimethyl ether/water without utilizing an alkali, as described in Japanese Patent Application Laid-Open No. H02-88569 and U.S. Pat. No. 4,977,283, has a very low yield of FDCA.

On the other hand, the method of oxidizing 5-HMF with nitric acid or dinitrogen tetroxide in DMSO as described in Annual report of the Noguchi Institute, vol. 22, pages 24 to 26 is high in energy consumption as the reaction is carried out at a high temperature, and has a very low yield of the FDCA. The method of oxidizing 5-HMF with potassium permanganate, utilizing pyridine as a base, as described in Toni EL HAJJ et al., Bulletin de la Societe de France, vol. 5, 1987 "Synthese de l'hydroxymethyl-5 furanne carboxaldehyde-2 et de ses derives par traitement acide de sucres sur resines echangeuses d'ions", p. 860, experimental C takes a long reaction time and has a yield of 70%. The method of dehydrating mucic acid by p-toluenesulfonic acid as described in Lewkowski J., Polish Journal of Chemistry, vol. 75, 2001 "Convenient Synthesis of Furan-2,5-dicarboxylic Acid and Its Derivatives" p. 1944 is high in energy consumption as the reaction is carried out at a high temperature, and has a yield of FDCA as low as 25%.

SUMMARY OF THE INVENTION

The present inventors consider that the temperature condition of 80° C. or higher is high in energy consumption and has room for improvement.

The present inventors consider that the reaction time of several hours is long and has room for improvement.

The present inventors consider that the yield of 70% is low and has room for improvement.

An object of the present invention is to provide a method for producing FDCA, capable of efficiently and quantitatively producing FDCA under mild conditions, without employing an expensive catalyst and with a reduced energy consumption.

The present inventors conducted exhaustive research on the method of producing FDCA under mild conditions and with a reduced energy consumption. As a result, it was found that FDCA can be produced efficiently and quantitatively under mild conditions and with a reduced energy consumption, by oxidizing a furan ring compound having specific substituent's with a permanganate metal salt in an alkaline environment, and on the basis of the finding, the present invention was made.

More specifically, the present invention provides a method for producing furan-2,5-dicarboxylic acid, which includes oxidizing, with a metal permanganate in an alkaline environment, a furan ring compound having two functional groups selected from a hydroxymethyl group, a formyl group and a carboxyl group at the 2- and 5-positions of the furan ring.

The method for producing furan-2,5-dicarboxylic acid of the present invention can efficiently and quantitatively produce FDCA under mild conditions, without employing an expensive catalyst and with a reduced energy consumption.

Further features of the present invention will become apparent from the following description of exemplary embodiments.

DESCRIPTION OF THE EMBODIMENTS

The method for producing furan-2,5-dicarboxylic acid of the present invention includes oxidizing a furan ring compound having two functional groups selected from a hydroxymethyl group, a formyl group and a carboxyl group at the 2- and 5-positions of the furan ring, by the use of a metal permanganate (or a permanganic acid metal salt) in an alkaline environment.

The furan ring compounds used in the method of the present invention for producing furan-2,5-dicarboxylic acid (FDCA):

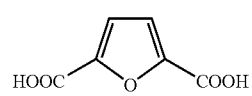

have two functional groups selected from a hydroxymethyl group, a formyl group and a carboxyl group at the 2- and 5-positions of the furan ring and are high in reactivity. Specific examples of the compound include 2,5-diformylfuran (DFF):

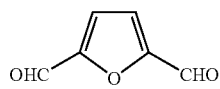

5-hydroxymethylfurfural (5-HMF):

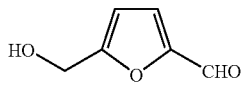

5-formylfuran-2-carboxylic acid (CFF):

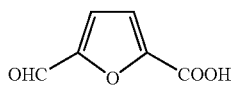

2,5-di(hydroxymethyl)furan:

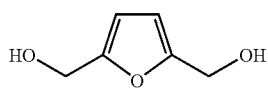

and 5-hydroxymethylfuran-2-carboxylic acid (HMFA):

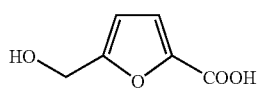

Among these, a compound having a formyl group is advantageous, and one or two or more of 5-hydroxymethylfurfural (5-HMF), 2,5-diformylfuran (DFF), 5-formylfuran-2-carboxylic acid (CFF) and 5-hydroxymethylfuran-2-carboxylic acid (HMFA) are particularly advantageous.

In the method for producing furan-2,5-dicarboxylic acid of the present invention, an alkaline environment for the furan ring compound may be realized, for example, by a method of using an alkali. Examples of the alkali to be used include alkali metal compounds, alkali earth metal compounds, an ammonium ion and other organic bases, and one or two or more of alkali metal hydroxides and alkali earth metal hydroxides can advantageously be employed. The alkali metal hydroxides include sodium hydroxide and potassium hydroxide, and the alkali earth metal hydroxides include barium hydroxide and calcium hydroxide. Among these, either one or a combination of sodium hydroxide and potassium hydroxide can advantageously be employed. Such alkali may be used as an aqueous solution.

Such alkali is preferably employed in an amount of 2 moles or more with respect to 1 mole of the furan ring compound, in order that the oxidation reaction can efficiently proceed. The amount of alkali is more preferably 4 moles or more with respect to 1 mole of the furan ring compound, and further preferably 10 moles or more.

The metal permanganate to be employed in the producing method for furan-2,5-dicarboxylic acid of the present invention may be any metal permanganates having an oxidizing power. The oxidative metal permanganates include a lithium salt, a sodium salt, a potassium salt, a rubidium salt, a cesium salt, a beryllium salt, a magnesium salt, a calcium salt, a strontium salt, a barium salt, a zinc salt and a silver salt of permanganic acid, and may be used singly or in a combination of two or more kinds. Such metal permanganates may be added as an aqueous solution to the reaction system, but is preferably added in a solid state to the reaction system, in order to prevent the concentration of a raw material from being reduced.

The amount of the metal permanganate may be suitably selected according to the type of furan ring compound. More specifically, in the case where the furan ring compound is 5-HMF, the amount is preferably in a range of from 1 to 5 moles with respect to 1 mole of 5-HMF. The amount of the permanganate metal salt equal to or larger than 1 mole with respect to 1 mole of 5-HMF can oxidize all the formyl groups and hydroxymethyl groups in 5-HMF. The amount of the permanganate metal salt equal to or less than 5 moles with respect to 1 mole of 5-HMF can prevent the furan ring compound or the produced FDCA from being decomposed, thus preventing the metal permanganate from being uselessly consumed. The amount of the metal permanganate is more preferably in a range of from 1.5 to 4 moles with respect to 1 mole of 5-HMF, and further preferably from 2 to 3 moles.

In the case where the furan ring compound is DFF, the amount of the metal permanganate is preferably in a range of from 0.7 to 3.5 moles with respect to 1 mole of DFF. The amount of the metal permanganate equal to or larger than 0.7 moles with respect to 1 mole of DFF can oxidize all the formyl groups and hydroxymethyl groups in DFF. The amount of the metal permanganate equal to or less than 3.5 moles with respect to 1 mole of DFF can prevent the furan ring compound or the produced FDCA from being decomposed, thus preventing the metal permanganate from being uselessly consumed. The amount of permanganate metal salt is more preferably in a range of from 1.0 to 2.8 moles with respect to 1 mole of DFF, and further preferably from 1.4 to 2.1 moles.

In the case where the furan ring compound is CFF, the amount of the metal permanganate is preferably in a range of from 0.4 to 2.0 moles with respect to 1 mole of CFF. The amount of the metal permanganate equal to or larger than 0.4 moles with respect to 1 mole of CFF can oxidize all the formyl groups and hydroxymethyl groups in CFF. The amount of the metal permanganate equal to or less than 2.0 moles with respect to 1 mole of CFF can prevent the furan ring compound or the produced FDCA from being decomposed, thus preventing the metal permanganate from being uselessly consumed. The amount of the metal permanganate is more preferably in a range of from 0.6 to 1.6 moles with respect to 1 mole of CFF, and further preferably from 0.8 to 1.2 moles.

In the case where the furan ring compound is HMFA, the amount of the metal permanganate is preferably in a range of from 0.7 to 3.5 moles with respect to 1 mole of HMFA. The amount of the metal permanganate equal to or larger than 0.7 moles with respect to 1 mole of HMFA can oxidize all the hydroxymethyl groups in HMFA. The amount of the metal permanganate equal to or less than 3.5 moles with respect to 1 mole of HMFA can prevent the furan ring compound or the produced FDCA from being decomposed, thus preventing the metal permanganate from being uselessly consumed. The amount of the metal permanganate is more preferably in a range of from 1.0 to 2.8 moles with respect to 1 mole of HMFA, and further preferably from 1.4 to 2.1 moles.

In the method for producing furan-2,5-dicarboxylic acid of the present invention, the furan ring compound, the alkali and the metal permanganate may be supplied in any order, but it is preferable to feed the furan ring compound into the aqueous solution of alkali. The amount of the alkaline aqueous solution is preferably in a range of from 5 to 500 parts by mass with respect to 1 part by mass of the furan ring compound. The amount equal to or larger than 5 parts by mass enables the reaction temperature to be easily controlled, and the amount equal to or less than 500 parts by mass allows the concentration of alkali to become suitable for efficient post-treatment. The range of from 10 to 200 parts by mass is more preferable, and the range of from 50 to 150 parts by mass is further preferable. Thereafter, the metal permanganate may be added to the alkaline aqueous solution containing the furan ring compound.

The oxidation reaction of the furan ring structure due to the metal permanganate in the alkaline aqueous solution may be carried out at a temperature of from 1 to 50° C., if necessary, under heating, but is advantageously performed at room temperature (about 25° C.) in order to reduce an energy consumption.

EXAMPLES

In the following, the method for producing furan-2,5-dicarboxylic acid of the present invention will be described in detail by means of examples, but the technical scope of the present invention is by no means limited to such examples.

The compounds used in Examples are the following commercial products: 5HMF: a reagent manufactured by Aldrich Inc., purity 99%; sodium hydroxide: manufactured by Kishida Chemical Co., G.R. (guaranteed reagent), purity 96%; potassium permanganate: manufactured by Kishida Chemical Co., G.R., purity 99.3%; and 2,5-diformylfuran (DFF): manufactured by Tokyo Kasei Co., purity 98%.

Example 1

In a solution (25° C.) prepared by dissolving sodium hydroxide (958 mg, 23 mmol) in water (10 g), then adding 5-HMF (126 mg, 1 mmol), crystals of potassium permanganate (363 mg, 2.3 mmol) were added under agitation, and the agitation was further continued for 10 minutes at room temperature. A precipitate of manganese oxide was filtered off, and a concentrated hydrochloric acid was added to the filtrate so as to bring the pH into 1 or less, thereby precipitating FDCA. The precipitate was separated by filtration, washed with water and dried to produce FDCA (132 mg, 0.85 mmol). The isolation yield was 85%.

Example 2

FDCA was produced in the same manner as in Example 1 except that 5 g of water was used for dissolving 5-HMF and 363 mg of sodium permanganate was substituted for 363 g of potassium permanganate. 126 mg of FDCA were obtained, with an isolation yield of 81%.

Example 3

FDCA was produced in the same manner as in Example 1 except that 363 mg of calcium permanganate was substituted for 363 g of potassium permanganate. 124 mg of FDCA were obtained, with an isolation yield of 79%.

Example 4

In a solution (25° C.) obtained by dissolving sodium hydroxide (958 mg) in water (10 g), then adding 2,5-diformylfuran (DFF) (124 mg), crystals of potassium permanganate (242 mg) were added under agitation, and the agitation was further continued for 10 minutes at room temperature. 139 mg of FDCA were obtained, with an isolation yield of 89%.

Comparative Example 1

FDCA was produced in the same manner as in Example 1 except that 43 mg of sodium hydroxide was substituted for 958 mg of sodium hydroxide. 107 mg of FDCA were obtained, with an isolation yield of 69%.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2006-088520 filed Mar. 28, 2006 which is hereby incorporated by reference herein in its entirety.

What is claimed is:

1. A method for producing furan-2,5-dicarboxylic acid comprising the steps of:
   dissolving a hydroxide in water to form an alkaline environment; and
   oxidizing a furan ring compound having two functional groups selected among a hydroxymethyl group, a formyl group and a carboxyl group in the 2- and 5-positions of the furan ring, with a metal permanganate in the alkaline environment,
   wherein the hydroxide is employed in an amount of at least 2 moles with respect to 1 mole of the furan ring compound.

2. The method for producing furan-2,5-dicarboxylic acid according to claim 1, wherein the furan ring compound is used in a state that it is contained in an alkaline aqueous solution.

3. The method for producing furan-2,5-dicarboxylic acid according to claim 1, wherein the hydroxide is at least one of an alkali metal hydroxide and alkali earth metal hydroxide.

4. The method for producing furan-2,5-dicarboxylic acid according to claim 3, wherein either at least one of sodium hydroxide and potassium hydroxide is used as the alkali metal hydroxide.

5. The method for producing furan-2,5-dicarboxylic acid according to claim 1, wherein the furan ring compound is at least one of 5-hydroxymethylfurfural, 2,5-diformylfuran, 5-formylfuran-2-carboxylic acid and 5-hydroxymethylfuran-2-carboxylic acid.

6. The method for producing furan-2,5-dicarboxylic acid according to claim 1, wherein the metal permanganate contains at least one metal selected from an alkali metal an alkali earth metal, zinc and silver.

7. The method for producing furan-2,5-dicarboxylic acid according to claim 1, wherein the metal permanganate contains at least one metal selected from potassium, sodium, calcium and barium.

8. The method for producing furan-2,5-dicarboxylic acid according to claim 1, wherein the metal permanganate is added to an alkaline aqueous solution containing the furan ring compound.

9. The method for producing furan-2,5-dicarboxylic acid according to claim 8, wherein the metal permanganate is in a solid state.

10. The method for producing furan-2,5-dicarboxylic acid according to claim 8, wherein the furan ring compound contains at least one of 5-hydroxymethylfurfural, 2,5-diformylfuran, 5-formylfuran-2-carboxylic acid and 5-hydroxymethylfuran-2-carboxylic acid.

11. The method for producing furan-2,5-dicarboxylic acid according to claim 1, wherein the oxidation is carried out at a temperature within a range of from 1° to 50° C.

* * * * *

UNITED STATES PATENT AND TRADEMARK OFFICE
CERTIFICATE OF CORRECTION

| | | |
|---|---|---|
| PATENT NO. | : 7,411,078 B2 | Page 1 of 1 |
| APPLICATION NO. | : 11/683271 | |
| DATED | : August 12, 2008 | |
| INVENTOR(S) | : Toshimari Miura et al. | |

It is certified that error appears in the above-identified patent and that said Letters Patent is hereby corrected as shown below:

<u>COLUMN 1</u>:

Line 9, "dicarboxlic acid" should read --dicarboxylic acid--; and
    Line 14, "Furan-2,5 -dicarboxylic" should read --Furan-2,5-dicarboxylic--.

<u>COLUMN 2</u>:

Line 29, "substituent's" should read --substituents--.

<u>COLUMN 6</u>:

Line 56, "2,5 -diformylfuran," should read --2,5-diformylfuran,--; and
    Line 57, "5 -hydroxymethylfuran" should read --5-hydroxymethylfuran--.

<u>COLUMN 8</u>:

Line 2, "5 -hydroxymeth-" should read --5-hydroxymeth- --.

Signed and Sealed this

Tenth Day of March, 2009

JOHN DOLL
*Acting Director of the United States Patent and Trademark Office*